(12) United States Patent
Stappenbeck et al.

(10) Patent No.: US 11,925,555 B2
(45) Date of Patent: Mar. 12, 2024

(54) DOUBLE STEERABLE SHEATH AND METHOD FOR DEPLOYMENT OF A MEDICAL DEVICE

(71) Applicant: TRICARES SAS, Paris (FR)

(72) Inventors: Nadine Stappenbeck, Aschheim (DE); Helmut Straubinger, Aschheim (DE)

(73) Assignee: TRICARES SAS, Paris (FR)

( * ) Notice: Subject to any disclaimer, the term of this patent is extended or adjusted under 35 U.S.C. 154(b) by 109 days.

(21) Appl. No.: 16/640,180

(22) PCT Filed: Aug. 22, 2018

(86) PCT No.: PCT/EP2018/072686
§ 371 (c)(1),
(2) Date: Feb. 19, 2020

(87) PCT Pub. No.: WO2019/038337
PCT Pub. Date: Feb. 2, 2019

(65) Prior Publication Data
US 2020/0360141 A1    Nov. 19, 2020

(30) Foreign Application Priority Data
Aug. 24, 2017   (EP) .................................... 17001430

(51) Int. Cl.
*A61F 2/24*    (2006.01)
*A61F 2/95*    (2013.01)
(Continued)

(52) U.S. Cl.
CPC .......... *A61F 2/2436* (2013.01); *A61F 2/9517* (2020.05); *A61M 25/0141* (2013.01);
(Continued)

(58) Field of Classification Search
CPC .......... A61F 2/2436; A61F 2210/0014; A61M 25/0141; A61M 25/0136; A61M 2025/015; A61M 2025/0161; A61M 2025/0681; A61M 2210/125; A61M 25/0662; A61M 25/0147
See application file for complete search history.

(56) References Cited

U.S. PATENT DOCUMENTS 9,402,976 B2 * 8/2016 Lam .................... A61B 18/1492
2002/0058858 A1 * 5/2002 Ogura .................... A61B 1/273
600/141

(Continued)

FOREIGN PATENT DOCUMENTS

| WO | 2008/118481 A1 | 10/2008 |
| WO | 2009/137712 A1 | 11/2009 |
| WO | 2016/090025 A1 | 6/2016 |

OTHER PUBLICATIONS

International Search Report, PCT Application No. PCT/EP2018/0726868 dated Dec. 3, 2018, 6 pages.

*Primary Examiner* — Kelly J Bekker
*Assistant Examiner* — Andrew P. Restaino
(74) *Attorney, Agent, or Firm* — The Dobrusin Law Firm, P.C.

(57) ABSTRACT

The present invention relates to a double steerable sheath, a delivery system comprising such a sheath and a method for deployment of a medical device, e.g. a replacement heart valve prosthesis, in a patient's heart.

25 Claims, 20 Drawing Sheets

(51) Int. Cl.
*A61M 25/01* (2006.01)
*A61M 25/06* (2006.01)

(52) U.S. Cl.
CPC . *A61M 25/0147* (2013.01); *A61F 2210/0014* (2013.01); *A61M 25/0136* (2013.01); *A61M 2025/0161* (2013.01); *A61M 2025/0681* (2013.01)

(56) References Cited

U.S. PATENT DOCUMENTS

| | | | |
|---|---|---|---|
| 2004/0049207 A1 | 3/2004 | Goldfarb et al. | |
| 2006/0041188 A1* | 2/2006 | Dirusso | A61B 1/0055 600/152 |
| 2007/0156116 A1* | 7/2007 | Gonzalez | A61M 25/0136 604/528 |
| 2007/0270679 A1* | 11/2007 | Nguyen | A61M 25/0141 600/373 |
| 2010/0022948 A1 | 1/2010 | Wilson et al. | |
| 2012/0209122 A1* | 8/2012 | Garbini | A61M 25/0147 600/466 |
| 2014/0187894 A1* | 7/2014 | Bui | A61B 5/4836 600/373 |
| 2014/0379000 A1* | 12/2014 | Romo | A61B 34/30 606/130 |
| 2017/0258614 A1* | 9/2017 | Griffin | A61F 2/966 |
| 2018/0049873 A1* | 2/2018 | Manash | A61F 2/2436 |
| 2018/0256851 A1* | 9/2018 | Edminster | A61M 25/0097 |

\* cited by examiner

116

DOUBLE STEERABLE SHEATH AND METHOD FOR DEPLOYMENT OF A MEDICAL DEVICE

FIELD

The present invention relates to a double steerable sheath, a delivery system comprising such a sheath and a method for deployment of a medical device, e.g. a heart valve prosthesis in a patient's heart.

BACKGROUND

In the last decades, minimally invasive techniques have advanced and are now possible in many medical fields.

In a number of medical fields, it is now possible to treat patients by minimally invasive techniques and allow for treatment of patients who could otherwise not be adequately treated due to their physical condition and the risks connected with surgery. Many of such minimally invasive methods apply delivery systems meant to deliver the medical device to a desired target site.

In particular, in recent years the treatment of heart valve diseases and defects has become more and more successful. Examples are transapical, transjugular and transfemoral procedures for heart valve replacement therapies, e.g. aortic or mitral heart valve treatments.

In many cases a stent-based prosthesis with a tissue based replacement valve is used and implanted to replace the native heart valve. The replacement heart valve is implanted by way of a catheter or delivery system.

The replacement heart valve has to be crimped and loaded onto the delivery system. The delivery system is then introduced e.g. into the patient's vasculature and directed to the target site. At the target site and due to the particular geometry of the patient the distal part of the delivery system carrying the replacement heart valve has to be positioned very precisely before deployment in order to achieve a correct deployment. A correct and precise deployment is very important for a successful function of the implanted device.

In known delivery systems various designs have been developed in order to provide a steerable distal part for a more precise deployment.

A correct deployment of a medical device is very complex as it has not only to be pushed through the vasculature of the patient, but it has to bend and progress to the target site including change of direction and changing angles. Finally, not only the correct site has to be reached but it is also desirable that a specific three dimensional positioning is achieved including inter alia the position as such, a certain angle and uniform distances from the native tissue in e.g. a cavity.

Hence there exists a need for a device which allows for precise three-dimensional positioning of its distal part carrying the medical device and allowing for a defined and controlled deployment of the medical device.

One problem in current delivery systems is that the medical device cannot be placed at the desired target site with good precision.

In particular it is a problem to position the distal part of a delivery system in a way so that one can achieve its positioning in all desired three-dimensional levels or/and the correct and desired positioning of the capsule carrying the medical device for the subsequent deployment step.

More particularly, it is a problem that even steerable solutions of the prior art do not allow for a desired and optimized positioning with regard to a certain angle of the replacement device and/or its distance to the native environment and/or a desired angle with regard to the deployment level.

Thus, in known delivery systems it is not possible to direct and locate the replacement device in its delivery system in an optimal three-dimensional position prior to the release step. This implies the disadvantage of an incorrect final implantation position and leads to a sub-optimal final positioning in the patient.

SUMMARY

Accordingly, it is one object to provide a means allowing for better delivery and a more precise positioning of the prosthesis at the target site, or at least to achieve reducing the disadvantages of the prior art or essentially avoiding these disadvantages.

It is another object to provide a means for better three-dimensional actuation and positioning of the medical replacement device before deployment, or at least reducing the disadvantages of the prior art or essentially avoiding their disadvantages.

It is another object to provide a means which can be combined with a delivery system for better three-dimensional actuation and positioning of the medical replacement device before deployment, or at least reducing the disadvantages of the prior art or essentially avoiding their disadvantages.

It is another object to provide a method for better three-dimensional actuation and positioning of the medical replacement device before deployment, or at least reducing the disadvantages of the prior art or essentially avoiding their disadvantages.

In one aspect the disclosure relates to a sheath designed to be double actuatable and double bendable in two different directions, e.g. essentially counter-bendable and double-actuatable.

In another aspect the disclosure relates to a delivery system composed of a double steerable or S-shaped steerable sheath and a delivery catheter for a medical device, e.g. a replacement heart valve.

In another aspect the disclosure relates to a system comprising a double or S-shaped steerable sheath, a medical device, e.g. as prosthesis a replacement heart valve, and a catheter.

In another aspect the disclosure relates to a method of three-dimensional positioning of the distal part of a steering sheath and/or a distal catheter capsule carrying a medical device, e.g. a heart valve, for improved deployment.

In another aspect the disclosure relates to a method of deploying a medical device at a target site in a patient, e.g. at a native heart valve which shall be replaced.

BRIEF DESCRIPTION OF THE DRAWINGS

Preferred embodiments of the disclosure are exemplified by the Figures wherein.

Left figure: The left image shows the ideal unidirectional sheath bending. This is targeted to be achieved by a pull wire running through the entire length of the steerable sheath, whereby a softer material is used on the distal end of the sheath and a harder material on the proximal side of the sheath. This, in theory causes to bend only the distal end of the sheath.

Middle figure: However, since the pull wire runs through the entire length of the sheath, it also has an effect on the entire sheath (image in the middle) and results in not only directing the tip of the sheath to bend but the entire sheath deflects forward. The proximal side of the sheath bends less due to the harder material, but still deflects slightly. This causes the tip of the sheath to dive downwards, not meeting the desired target point.

Right figure: the right image shows a preferred embodiment according to the disclosure of the invention wherein a second, counter-acting bend is introduced; advantageously it can be achieved to even out the unwanted bend of the proximal end of the sheath, so that the desired target point can be met with the sheath tip in a desired three-dimensional position.

Figure 1:
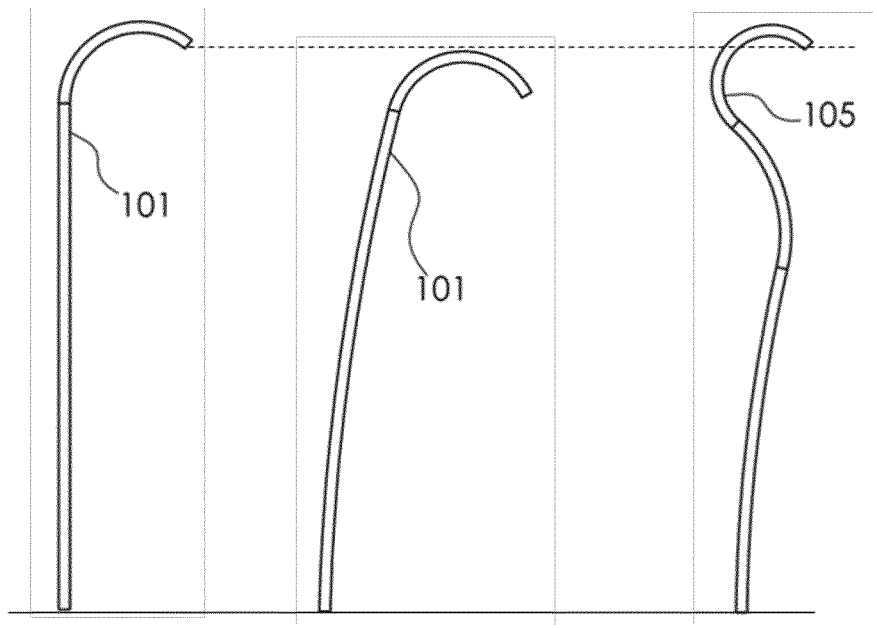
FIG. 1 illustrates a steerable sheath with ideal bending compared to the state of the art and an embodiment according to the disclosure of the invention.
Figure 2:
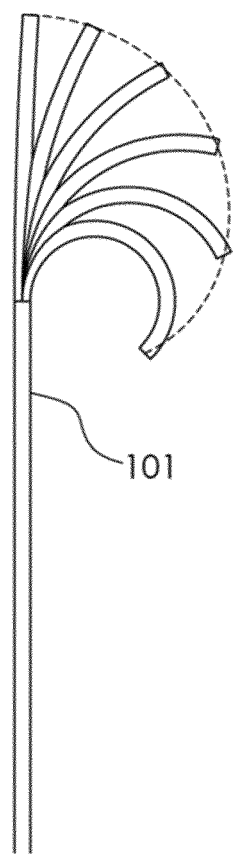

FIG. 2 illustrates bending possibilities of a steerable sheath according to the state of the art:

The figure shows the range of bends a sheath can achieve with unidirectional bending achieved by one pull wire. This design can only reach one target point per horizontal and vertical plane.

Figure 3:
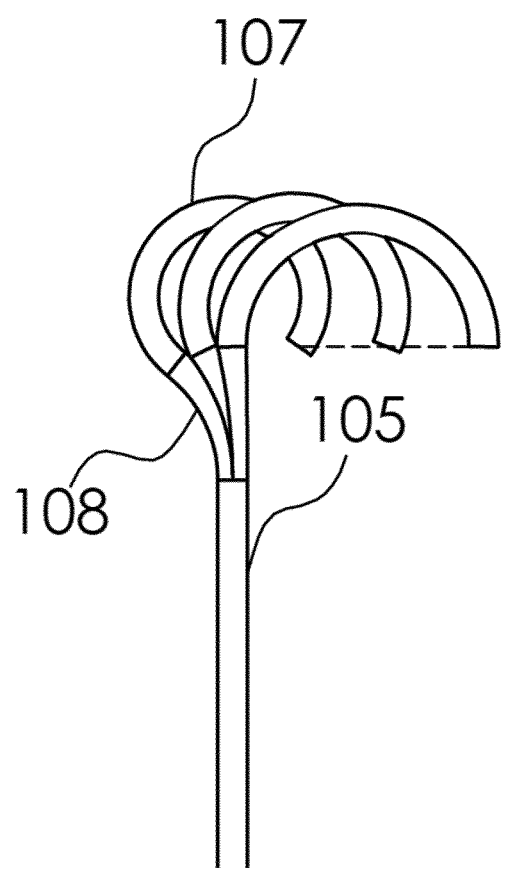

FIG. 3 illustrates a preferred embodiment according to the disclosure:

Incorporating a counter-acting bending mechanism advantageously allows to reach various target points within one horizontal plane by adjusting both bends.

Figure 4:
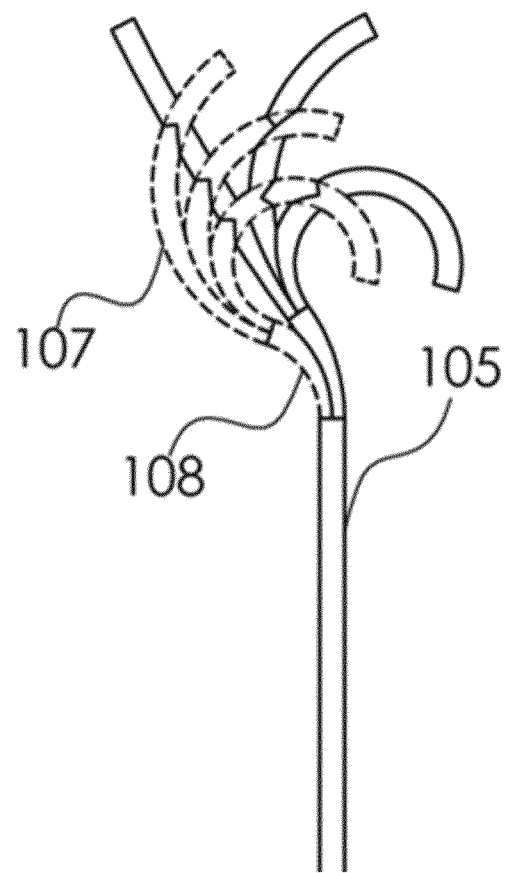

FIG. 4 illustrates a preferred embodiment according to the disclosure:

Adjusting the distal and proximal bend allows to reach even more potential target points. Moreover, by actuating both bends a smaller overall radius can be achieved, which advantageously allows bending in smaller anatomies.

Figure 5:
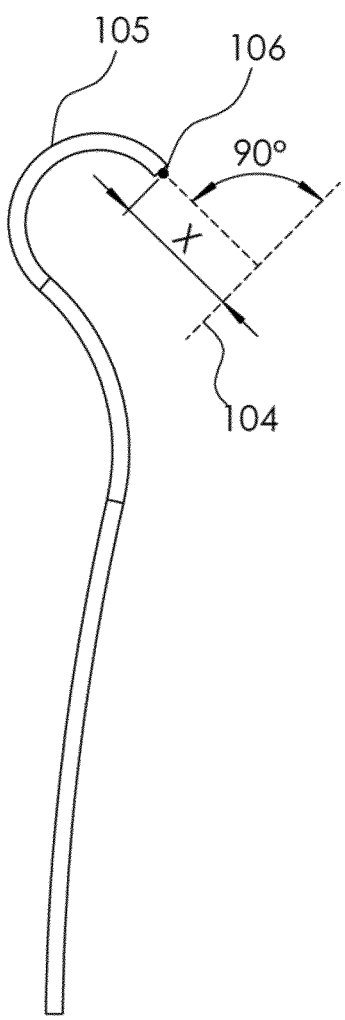

FIG. 5 illustrates a preferred embodiment according to the disclosure:

Typically, when deploying an implant, e.g. heart valve prosthesis, the best position for the delivery system is to be perpendicular (90°) to the implantation site (104)—which can also be denoted implantation level. This ensures that the implant is not deployed tilted. A certain predefined distance between the distal end of the steerable sheath and the implantation site is required to allow for unimpeded deployment by a catheter carrying the medial device, i.e. avoiding that the implant is being deployed into the sheath. The length "X" is therefore determined by the crimped length of the medical device, e.g. within a capsule of the catheter. The distal end of the steerable sheath (105) can be directed by the double steering of sheath (105) to the desired target point (106). Thus, the invention achieves advantageously that the catheter having mounted thereon a medical device can be pushed distally out of the steerable sheath and positioned correctly at the target level (104). Moreover, the double steering sheath according to the disclosure now allows for sufficient space for optimized three-dimensional positioning and easy release and deployment of the medical device, e.g. a replacement heart valve.

Figure 6:
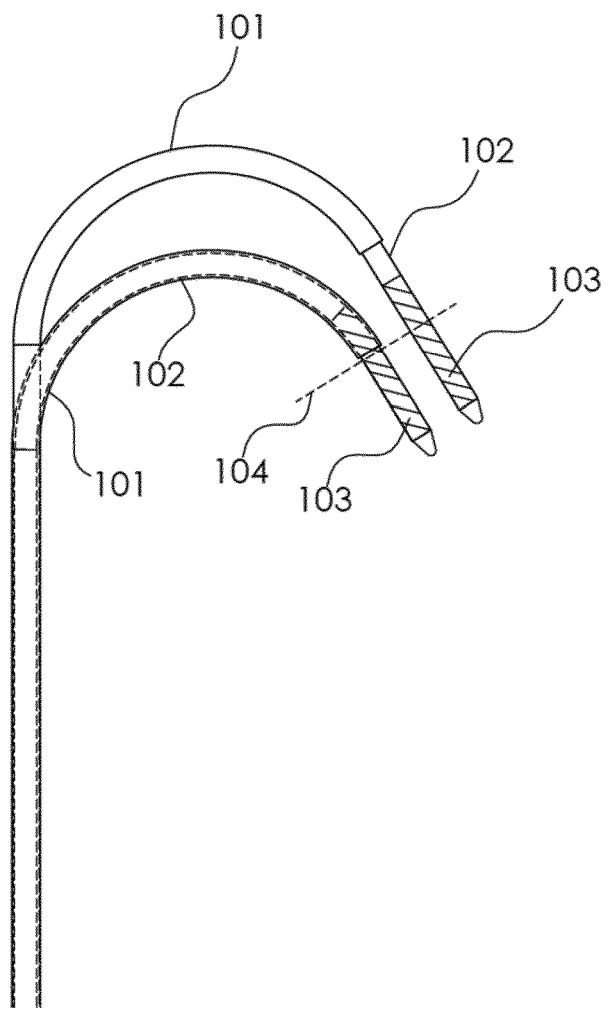

FIG. 6 illustrates an embodiment according to the prior art of a unidirectional steerable sheath;

The limitations in terms of positioning with a unidirectional sheath are shown. Important are (i) central alignment of the delivery system (102) within the implantation site (104), (ii) perpendicular orientation to the implantation site (90°) and (iii) a predefined distance ("X" as shown in FIG. 5) between the distal end of the steerable sheath (101) and the implantation site (104) to ensure unobstructed deployment of the medical device or implant (103). The lower sheath (101) including the catheter (102) in the image is centrally aligned within the implantation site. However, the distal end of the sheath (101) is right at the implantation site, which would cause the medical device (103) to be deployed into the sheath (101) and thus it cannot be freely released nor deployed correctly. Moving the sheath up facilitates the required distance between the distal end of the sheath (101) and the implantation site (104). However, with that the delivery system (102) loses its central alignment within the implantation site (104). If the bend was actuated further (not shown in image) the delivery system could be positioned to cross through the center of the implantation site, but not at a 90° angle.

Figure 7:
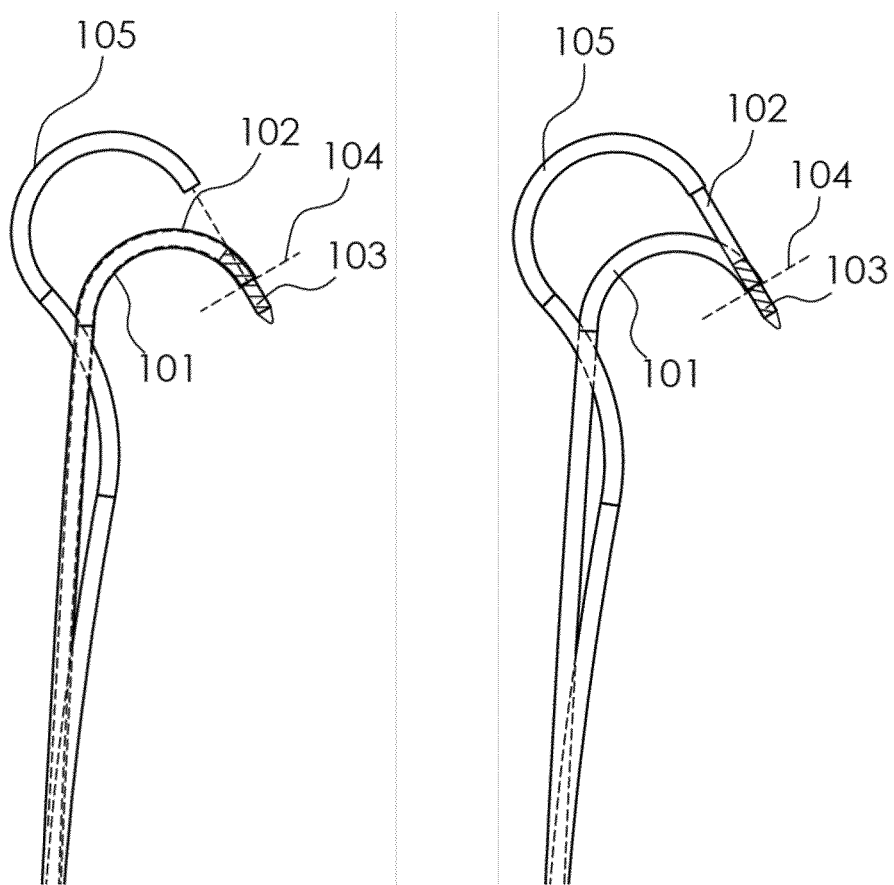

FIG. 7 illustrates a preferred embodiment of a double steerable sheath according to the disclosure (upper sheath) compared to a unidirectional sheath of the prior art (lower sheath):

The Figure shows a direct comparison between a unidirectional sheath (101) and a S-shaped steering sheath (105). The unidirectional sheath (101) can achieve a central position within the implantation site. However, due to its bending over the entire length (as described earlier with regard to the state of the art) the distal end of the sheath ends up at the level of the implantation site. This would result in the implant being deployed inside the sheath (101) because the catheter (102) has not fully parted from the distal part of the sheath (101) and thus the capsule carrying the medical device (103) is still at least partly within the sheath (101).

In comparison, the S-shaped steering sheath (105) can achieve a central and perpendicular alignment to the implantation site (104) or implantation level, and maintain the required distance between its distal end and the implantation site (104) and thus allow for easy release and improved deployment.

Figure 8:
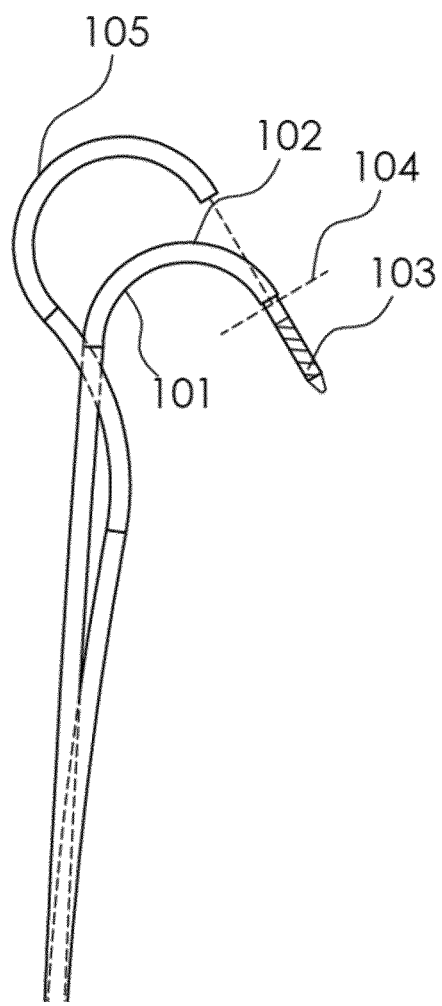

FIG. 8 illustrates a preferred embodiment of a double steerable sheath according to the disclosure (upper sheath) compared to a unidirectional sheath of the prior art (lower sheath):

The Figure shows a single bend sheath (101), which due to the slight bending over its entire length ends up at the implantation site or level (104) with its distal end, rather than at the target point, e.g. 20 mm above the annulus if a heart valve is targeted. Even though this position is perpendicular to the implantation site (104) and in the center, the implant (103) is now too low to be deployed.

It is noted that the implantation level (dashed line 104) should be at the center of the prosthesis in order to achieve an optimal deployment. On a practical level if the catheter (102) is retracted in a manner so that the center of the implant aligns with the target level (104) one aims at targeting, then the prosthesis is still at least partly covered by the sheath and cannot be released and cannot be deployed. Only by use of the double steering sheath (105) according to the disclosure one can position the end of the steering sheath (105) at a correct distance with enough space to position the catheter (not shown) with the capsule carrying the medical device to be deployed at the right level (104) and having enough space to release and deploy the implant.

Figure 9:
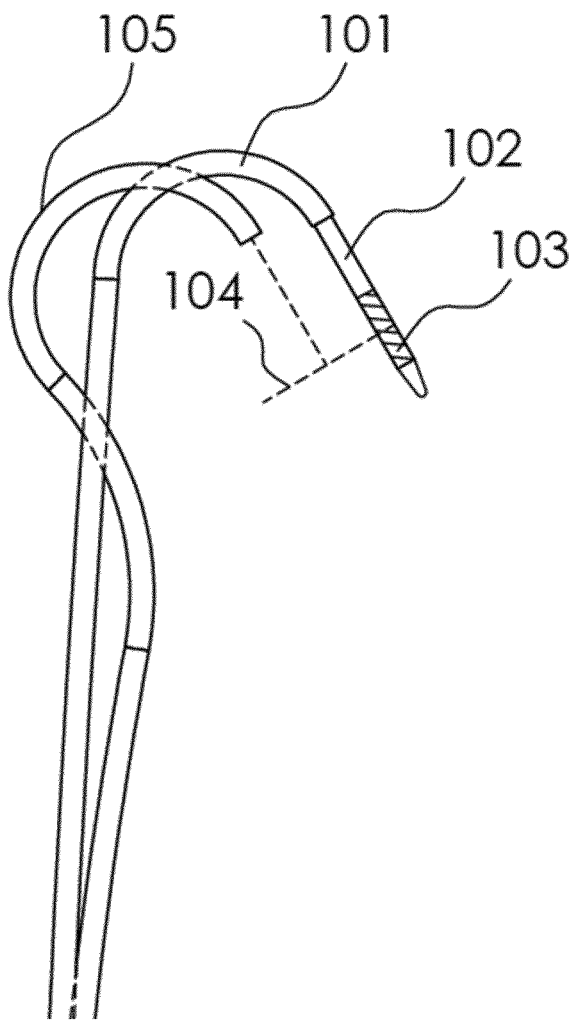

FIG. 9 illustrates a preferred embodiment of a double steerable sheath according to the disclosure (105) compared to a unidirectional sheath of the prior art (101):

This Figure shows that the single bend sheath (101) of the prior art can be moved up to achieve the 20 mm distance to the annulus/implantation site/level (104). However, by doing so the implant (103) is off center as the effect of the bending over the entire length of the sheath gets more obvious. In contrast and comparison, the double steerable sheath (105) can be centered and keep the required distance with regard to the implantation level (104) allowing advantageously for a free release and correct positioning and deployment of the medical device (103) (not shown here).

Figure 10:
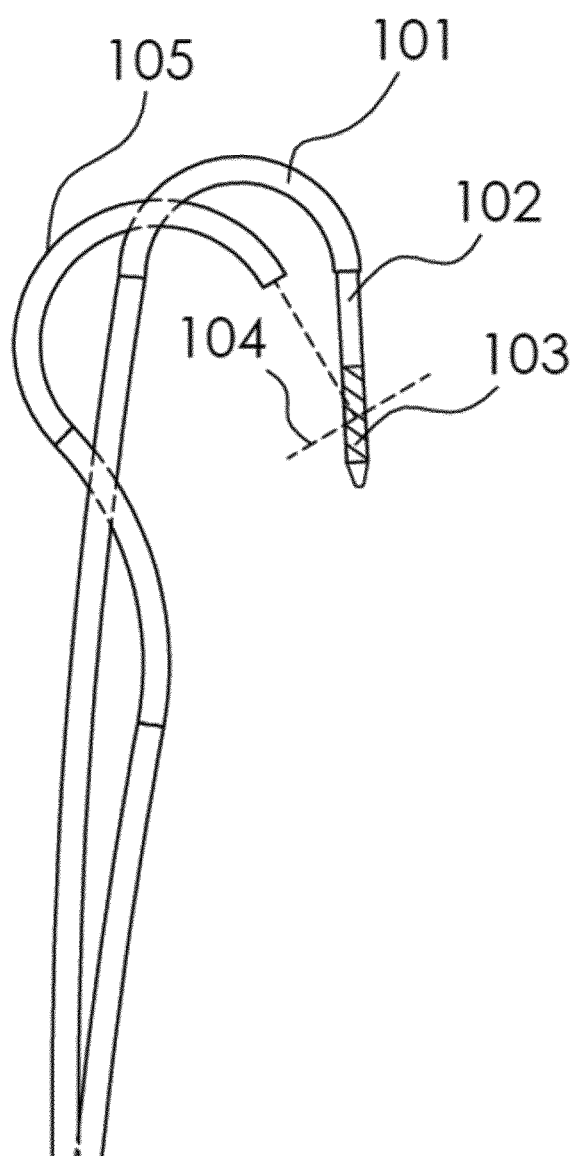

FIG. 10 illustrates a preferred embodiment of a double steerable sheath according to the disclosure (105) compared to a unidirectional sheath of the prior art (101):

Based on the previous FIG. 9 the single bend sheath (101) of the prior art could be actuated further to bring the prosthesis (103) to the center of the implantation site (104). However, at this point the prosthesis (103) will not be rectangular (90°) to the implantation site. Thus, it will not be possible to deploy the prosthesis (103) from the catheter (102) but in a tilted way with negative implications for its final positioning within the patient.

Figure 11A:
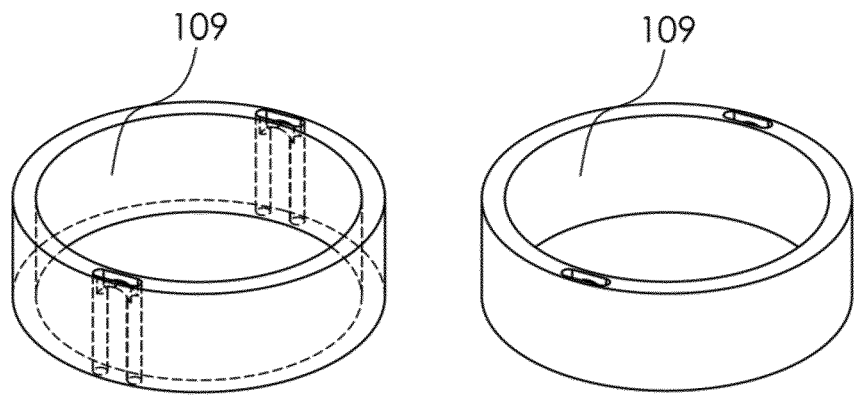
Figure 11B:
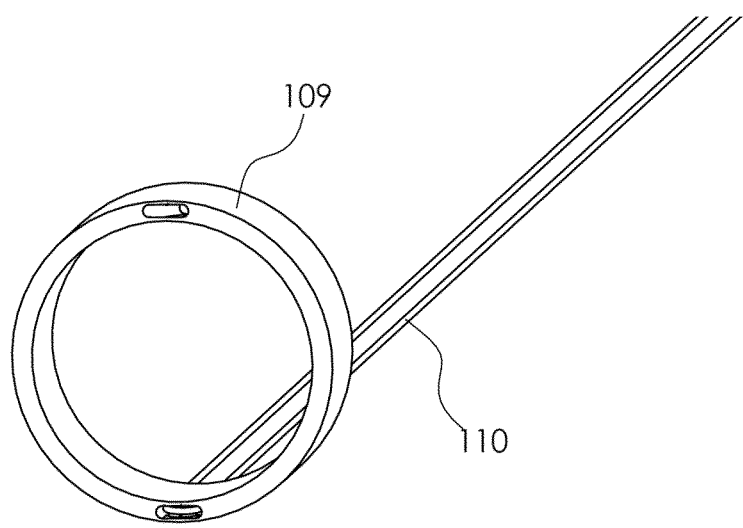

FIGS. 11a and 11b illustrate the attachment of a pull cable (110) at the pull ring (109) which will be fixed within the steerable sheath (105) according to the disclosure of a preferred embodiment of the disclosure:

In FIG. 11a depicts a pull ring (109) exhibiting two times two holes next to each other at different parts of the pull ring one representing the steering point. The cable is inserted in [NS1] one hole from the proximal side of the pull ring, then looped in the other hole from the distal side of the pull ring and thus a double cable is created in pull direction without the need of a fixing means at the pull ring. The pull cable attached to the distal pull ring can pass through the two holes which are not used in the proximal pull ring.

In an alternative embodiment the pull ring, or at least the proximal pull ring, can be designed as a e.g. 330° ring with two holes at one position and an opening on a second position; the opening is advantageously for passing through the distal pull cable/wire attached to the distal steering point without interfering with the proximal pull ring and giving enough space for the distal pull cable/wire. The pull ring can however also be designed as e.g. 270° or variations between 270° and 330°, as e.g. 290°, 300°, 310°.

In FIG. 11b a pull ring (109) exhibiting two holes including a pull cable (110) is depicted wherein the pull cable (110) is placed through the holes in opposite directions and thus serving as attachment for pulling the pull ring (109) and thus the steerable sheath in the respective direction.

Figure 12:
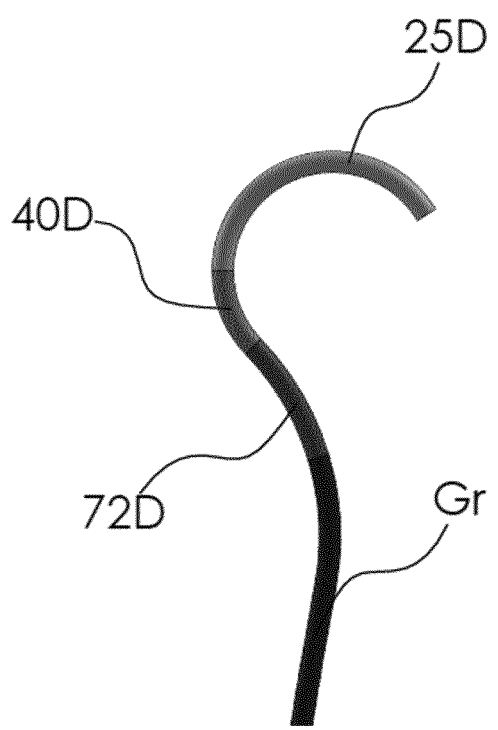

FIG. 12 illustrates a preferred embodiment of the disclosure and the use of different materials (25D, 40D, 72D, Gr) in the steerable sheath (S-shaped sheath) adapted to specific bending requirements as desired and which can be varied in order to achieve specific bending characteristics:

Proximal Grilamid® is used because it is a relatively stiff material. Further distal at defined sections different stiffness of Pebax® is used. 72D, 40D and 25D refer to different stiffness of the material. Here it is chosen to be more and more soft in distal direction. A polymer jacket is thus formed and used including reinforcement which is chosen according to the bending requirements of the device, i.e. bending radius and bending angle.

Distally included are laser cut hypotubes (115). Each direction of the S-shaped sheath (105) shows its specific hypotube depending on the intended bending direction. Distally on each of the hypotubes a pull ring (109, 111) is positioned for pull wire connection. The proximal part of the steerable sheath exhibits a braiding. Inside a PTFE liner can be added to reduce friction when operated in connection with a catheter.

Figure 13:
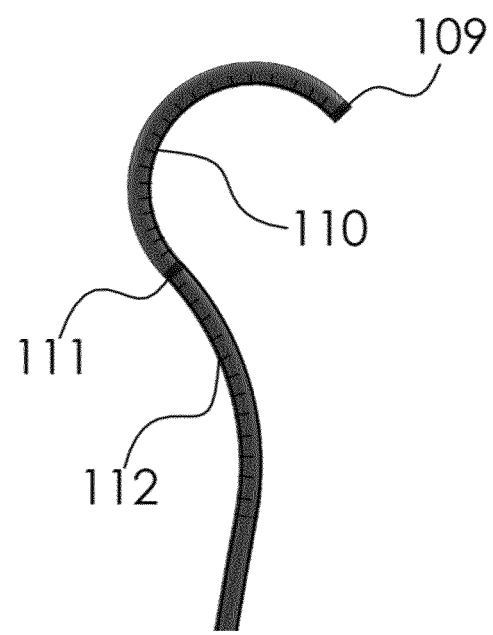

FIG. 13 illustrates two hypotubes and material aspects of a preferred embodiment of the disclosure:

In this case the cutting of the hypotube(s) are in an angle of 180° which allows for direct counter bending. The cutting can be made in one or two hypotubes wherein two hypotubes are combined by e.g. a polymer jacket. The pull rings (distal 109; proximal 111) and respective pull cables (110; 112) are shown.

Figure 14:
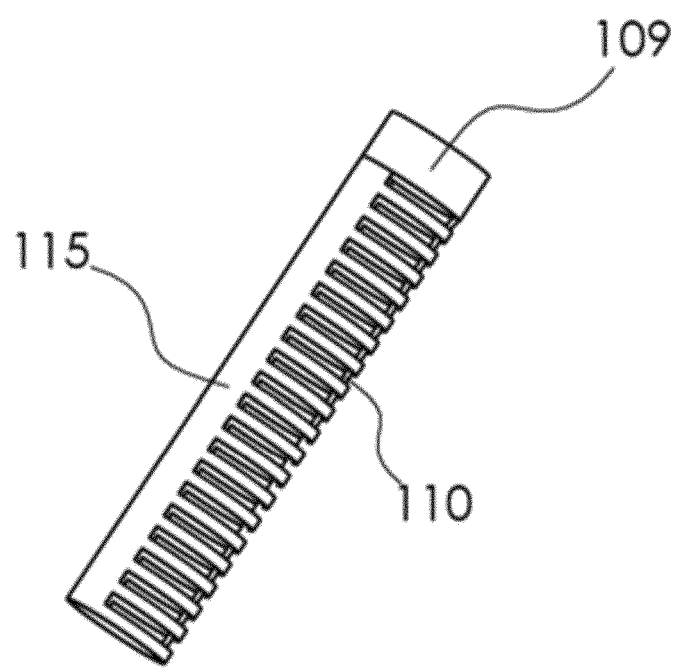

FIG. 14 illustrates a hypotube (115) of a preferred embodiment of the disclosure:

The distal pull ring (109) and the pull wire or cable (110) is indicated wherein the pull wire (110) runs inside the hypotube (115).

Figure 15:
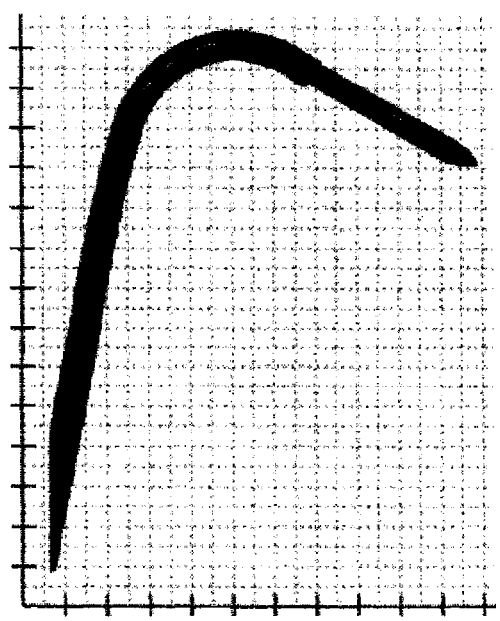
Figure 15B:
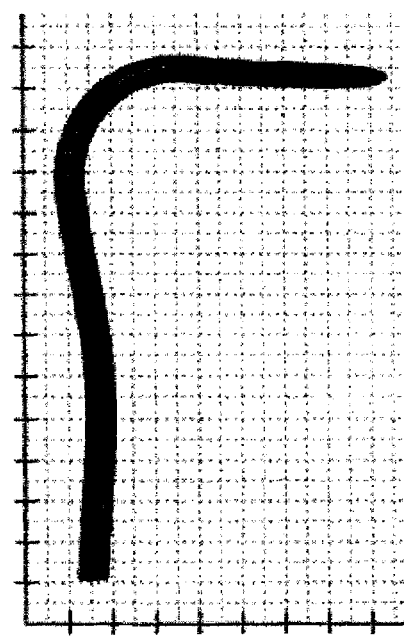
Figure 15C:
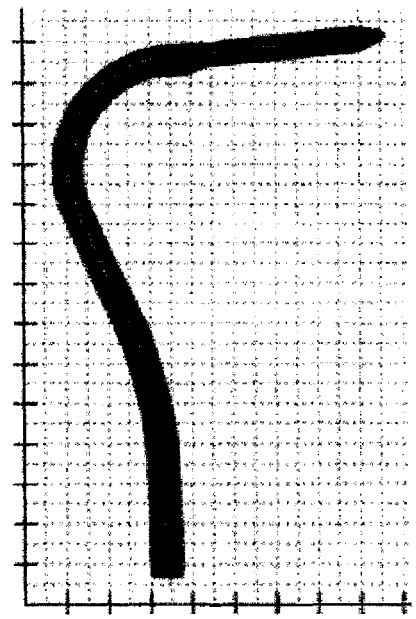

FIG. 15a-15c illustrate different bending states of the steerable sheath according to a preferred embodiment of the disclosure:

In FIG. 15a only the distal bending mechanism is operated by which only the distal bend is effected, however, also some parts of the proximal part are bend as a secondary effect leading to a rightward bending.

In FIG. 15b also the proximal cable is pulled to a certain degree leading to a partly counter-bending. Pulling further at the proximal pull cable a S-curve can be achieved (FIG. 15c). Also, the distal part of the sheath can be further pulled by distal pull cable (110) via distal pull ring (109) (not shown) and thus actuated to bend.

Figure 16:
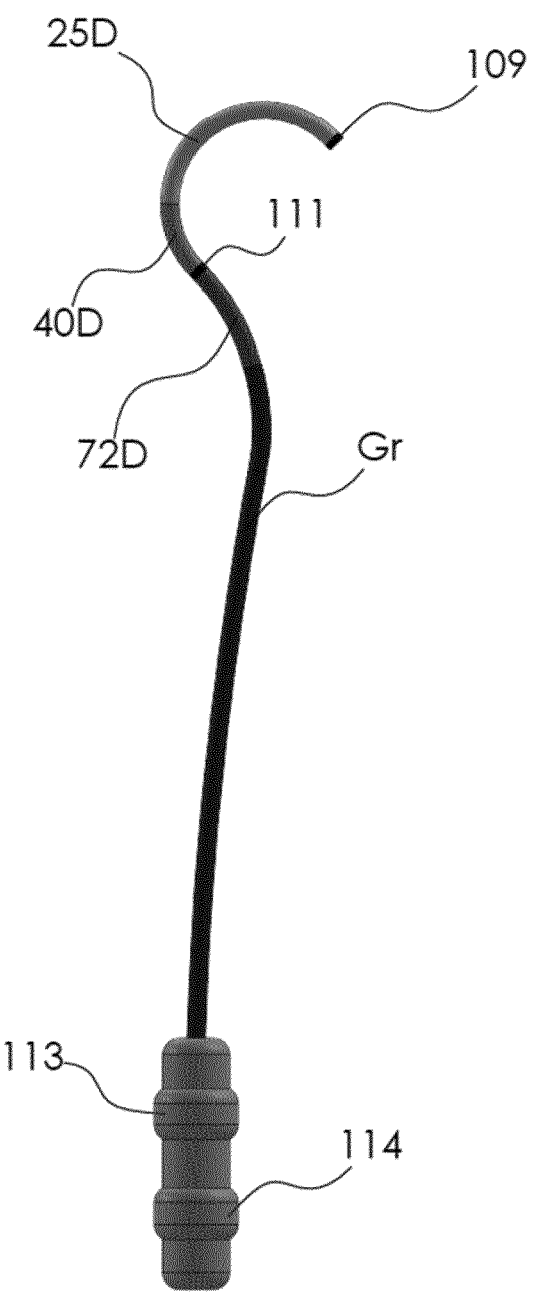

FIG. 16 depicts a preferred embodiment with the aspect of a steerable sheath according to the disclosure connected to a handle with at least two or two actuators (113, 114). The actuators are used to operate the double steering of the steering sheath. The different materials (25D, 40D, 72D, Gr) and pull rings (109, 111) are indicated.

Figure 17:
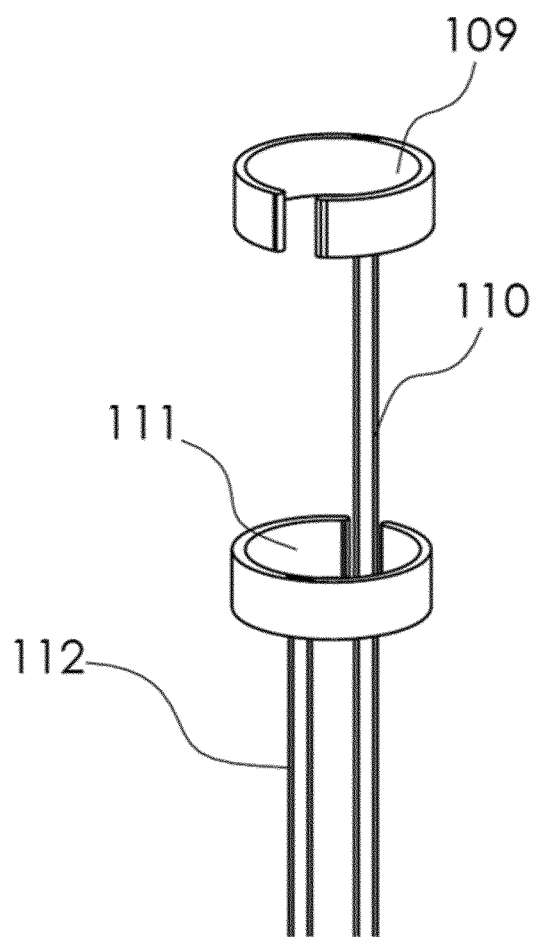

FIG. 17 depicts a distal pull ring (109) and a proximal pull ring (111) and cable (110) of distal pull ring and cable (112) of proximal pull ring wherein the cable (110) passes through the open space of the pull ring (111). The advantage being that there is no additional space in diameter needed and interference of the cable or wire with the proximal pull ring (111) is avoided.

Figure 18:
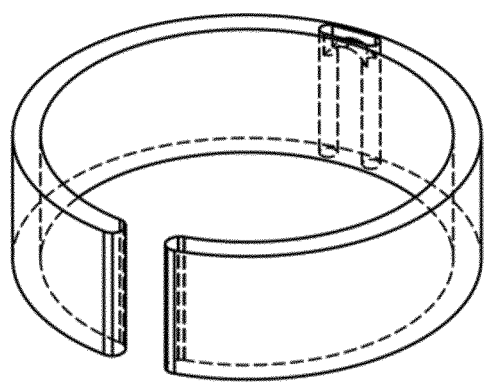

FIG. 18 depicts a drawing with hidden edges visible[NS2] of pull rings (109/111) of FIG. 17 exhibiting two holes at one position for attachment of a pull cable, and an open space (116) of the pull ring (109/111) for passing any sort of cable or wire from distal to proximal and possibly the handle of the device without any interference with said pull ring (111).

DETAILED DESCRIPTION

In the following certain terms of the disclosure will be defined. Otherwise technical terms in the context of the disclosure shall be understood as by the applicable skilled person.

The term "prosthesis" or "medical device" or "implant" in the sense of the disclosure is to be understood as any medical device that can be delivered in a minimally invasive fashion. The terms can be used interchangeably. It can be e.g. a stent or stent-based prosthesis or stent-based replacement heart valve like an aortic heart valve, a mitral heart valve or a tricuspid heart valve.

The term "catheter" or "delivery device" in the sense of the disclosure is to be understood as the device used to deploy a prosthesis in a patient at a determined site, e.g. to replace a heart valve like an aortic heart valve, a mitral heart valve or a tricuspid heart valve.

"S-sheath" or "S-shaped sheath" or "steerable sheath" or "double steerable sheath" or "S-shaped steering sheath" or "S-shaped steerable sheath" or "double steerable sheath" refer to a specifically steerable sheath which is actuated at at least two points, e.g. at two points or two steering points, and achieves a specific and directed essentially precise positioning of a replacement medical device. The terms can be used interchangeably. It may also have multiple steering points, e.g. three or four steering points and thus can be denoted a "multiple steerable sheath".

The term "pulling means" or "pull wire" or "pull cable" in the sense of the disclosure is to be understood as any means or part useful to exhibit a pulling force, e.g. a wire or cable.

The term "loading" in the sense of the disclosure is to be understood as positioning a prosthesis onto a catheter in a manner so that the catheter is ready to initiate a delivery and deployment procedure to a patient.

The term "useful material" in the sense of the disclosure is to be understood as any materials that are compatible with each other and possibly can be sterilized and/or are low friction materials.

An "elongate sheath" in the sense of the disclosure is a tube which can be made of different materials and which is biocompatible in the sense that it can be used for medical devices. The sheath can be composed of a combination of materials providing for a desired stiffness and/or flexibility as usually applied in catheter technology and known to the skilled person.

An "actuator" in the sense of the disclosure is a means which allows to operate a part distal from the actuator wherein e.g. the actuator is proximal and positioned on a handle and the part to be operated is distal and a means connects the two parts, e.g. a pull wire. One actuator can be designed in a manner so to actuate two parts simultaneously or sequentially or independently from each other. Alternatively, two actuators can each actuate one distal part in a coordinated manner, or the two actuators can also be linked in a manner to simultaneously or sequentially actuate the distal parts.

A "steering point" in the sense of the disclosure is a target point of the means that connects the actuator with the distal part which is meant to be operated. At a desired steering point one can e.g. attach a pull ring for connection with a pull wire which in turn is actuated by way of an actuator. Two or three or four steering points can be comprised in a steering sheath according to the disclosure of the invention wherein the steering points can be positioned according to the desired double bending for the sheath. The steering points can e.g. be spaced apart and they can be positioned in a certain angle to each other on the sheath, e.g. 180° or 90°. In case the steerable sheath contains two or three steering points they can be actuated independently, sequentially or simultaneously by way of one or two actuators.

"Unwanted secondary bending" in the sense of the disclosure is a movement of a sheath or catheter which is actively deflected in one direction and wherein due to said deflection and due to the flexibility of the sheath or/and catheter another part thereof also bends as a consequence. Such a secondary bending usually is unwanted, however, due to material characteristics it occurs and it impacts negatively on the positioning procedure and accuracy.

An "actuator" in the sense of the disclosure is a means which is connected by e.g. a pull wire with the pull ring and it serves to operate the pull ring, e.g. by applying tension on the pull wire which is connected to the pull ring, in order to bend the steering sheath in a predefined direction. One actuator can operate one pull ring and a steering sheath can contain a handle having one, two or more actuators wherein one actuator independently operates one pull ring via e.g. a pull wire, or one actuator can be designed to operate two pull rings and e.g. counter operate two pull rings by way of e.g. a pull wire wherein one pull wire is connected independently with one pull ring (i.e. at the steering point). The actuator serves to operate the steering sheath in a manner to direct the distal tip to a certain target point on a certain target level in the target area.

"Counter-actuating" in the sense of the disclosure relates to the coordinated bending of the steerable sheath depending on the placement of the e.g. pull ring and the position of the connection to the e.g. pull wire which results in bending and counter-bending. In case of 180° positioning of the two pull ring connecting points with the e.g. pull wire and a spacing on the steerable sheath on the longitudinal direction a counter-bending or counter-actuating as depicted in FIG. 15c creates a S-curve of the sheath.

The "target area" in the sense of the disclosure is the three dimensional space surrounding or being within the native organ like a native heart valve which can be e.g. a tricuspid heart valve.

The "target level" in the sense of the disclosure is the two dimensional level to which the steering sheath is meant to direct a certain portion of either the steering sheath itself or a distal catheter part, e.g. the capsule carrying a medical device e.g. a heart valve prosthesis. The "target level" can be the annulus level of the native heart valve.

The "target point" in the sense of the disclosure is the precise point on the target level which shall be reached with a specific part of the catheter and a specific area of the distal part of the catheter like the capsule carrying the medical device. The "target point" in a specific case can be the point which shall be reached by the distal end of the steerable sheath.

"Bending point" in the sense of the disclosure is the point in the sheath which bends depending on the materials and the laser cut hypotube and it can be defined by the polymer jacket and laser cut pattern accordingly, or it can be any useful material which serves the purpose of the disclosure like e.g. any way of reinforcement can be used e.g. braiding with differing PPIs or coils exhibiting different material characteristics.

In one aspect the problem underlying the application is solved by a steerable sheath comprising an elongate sheath, at least one actuator, at least two different sheath steering points, means for connecting the at least one actuator with the two different sheath steering points. The steering sheath can also be denoted a double steerable sheath.

The invention achieves in an advantageous manner to position a defined point or area of the steering sheath or/and a defined point or area of the distal part of a catheter introduced through the steering sheath into a patient at a target point in a target area. Thus by use of the steering sheath according to the disclosure it becomes possible to deploy a medical device, e.g. a heart valve prosthesis like a tricuspid heart valve prosthesis, very precisely in a three dimensional space and hence to achieve an optimized deployment of said medical device in a patient.

Thus it will become possible to precisely direct a certain level or point of the medical device, e.g. a replacement heart valve, to a certain level of the target site and thus e.g. align the replacement heart valve leaflets fixed to the replacement prosthesis with the annulus and/or with the leaflets of the native heart valve.

The steering sheath according to the current disclosure avoids at least partially or essentially entirely the disadvantages of known deployment systems for minimally invasive deployment of medical devices.

The steering sheath according to the current disclosure can be actuated advantageously in various three dimensional directions in a three-dimensional target area. It is thus possible to manoeuver the distal sheath and the distal catheter part carrying the medical device with regard to the desired position, level and angle to the target site. Accordingly, a deployment of the medical device with optimized alignment with regard to the native organ, e.g. a heart valve and its target level like the annulus, can thus be achieved and an optimized deployment will be possible.

The invention achieves advantageously that it is possible to position the distal part of the sheath or the distal part of a catheter pushed in distal direction inside the sheath in various levels and to a target point within the three-dimensional area of a target area. Thus, the invention allows to directing the distal part of the sheath or catheter essentially in three dimensions in a target area. The described advantages with regard to three-dimensional positioning are e.g. apparent from FIGS. 5 to 10 and 15.

The distal part may be actuated by known means which can be connected with a proximal handle. In preferred embodiments the steerable sheath may be connected with at least one actuator, e.g. the actuator(s) can be part of a handle for easier operation. The steerable sheath according to the disclosure can comprise two, three or four actuators, preferably wherein one actuator is independently connected with one sheath steering point or wherein two independent actuators actuate two steering points independently.

The steerable sheath according to the disclosure can be combined with a proximal handle and the actuator is combined with a proximal handle.

The handle can carry the actuator and a mechanism as known by the skilled person like a thread or lever to actuate the pull wire or any other known useful pull mechanism. The steerable sheath according to the disclosure may exhibit a useful number of steering points to actuate the sheath as desired in at least two directions independently or simultaneously or sequentially wherein the at least two sheath steering points are located distal. The steering point positions are chosen in order to achieve a two way bending wherein the bending is in principle a counter-bending to one another in order to compensate for unwanted secondary bending. In addition, the inventive concept of at least two steering points allows for precise actuation of the distal part of the sheath in the target area in a three dimensional space.

A steerable sheath according to preferred aspects of the disclosure may be built from one or more materials. The materials may be combined in a way so to advantageously support the desired bending and counter-bending of the sheath. The elongate sheath may be made of or comprises a combination of materials selected from biocompatible materials, Polytetrafluoroethylene (PTFE), polymers with differing durometers, stainless steel, nitinol, PEBAX®, or/and a polyamide, e.g. Grilamid®.

A softer and harder material may be combined to support the desired functionality of deflecting the sheath and a catheter contained therein. A steerable sheath according to the disclosure may be designed wherein a softer material is used on the distal end of the sheath and harder material on the proximal side of the sheath, preferably stainless steel, PEBAX®, preferably Grilamid®.

In a particular embodiment according to the disclosure the invention relates to a steerable sheath comprising two actuators, two steering sheath points, two means for connecting each of the actuators independently with each one of the sheath steering points.

A steerable sheath according to the disclosure can use any means compatible with the other parts and components for actuating and operating a distal steering point wherein the means for connecting is e.g. a wire, e.g. a flat wire, a round wire, a cable, a filament, or a tissue.

Each of the steering points can be connected with an actuator, preferably two, three or four actuators, i.e. each with its actuator, in different manners and it is possible to pull each steering point thus actuating the steerable sheath in various directions or a combination of directions using two, three or four steering points as is useful for operating the sheath and thus directing a defined point of the steerable sheath or/and catheter contained therein to the desired target point. A steerable sheath according to the disclosure can contain means for connecting which can be pulled proximally by way of one or more actuators.

The steering points as pointed out above can be positioned as is useful to achieve a specific deflection. A steerable sheath according to the disclosure can contain at least two to several steering points wherein the at least two different sheath steering points are spaced circumferential around the sheath or/and longitudinally along the sheath.

In specific embodiments of the disclosure a steerable sheath may comprise or exhibit two, three, or four sheath steering points, preferably two sheath steering points.

It may be advantageous to design a specific pattern of steering points on the steerable sheath. A steerable sheath according to the disclosure may have at least two or two different sheath steering points and wherein the steering points are spaced in an angle of 10°, 20°, 30°, 45°, 90°, 120°, 140°, 160°, or 180°.

Moreover, in a steerable sheath according to the disclosure at least two or two different sheath steering points are spaced with a distance of 1, 2, 3, 4, 5, 6, 7, 8, 9, or 10 cm. The spacing is at a certain angle as pointed out above and can be combined with a certain distance circumferentially or longitudinally.

Thus, a preferred embodiment of the disclosure is a steerable sheath wherein the at least two different sheath steering points are spaced in a combination of a 180° angle and a distance of about 15 to 40 cm, more preferably 15 to 20 cm.

It has been shown to be advantageous if a steerable sheath according to the disclosure exhibits two different sheath steering points located in an angle of 180° or in an angle of 180° and with a spacing of 5 to 10 cm, preferably 7 cm or 8 cm.

The steering points when actuated move in a coordinated manner. A steerable sheath according to the disclosure is characterized in that the two different sheath steering points are counter-acting movable by way of the two actuators.

It has proven very advantageous to design a steerable sheath according to the disclosure wherein two counter-acting actuators allow to reach various target points or preferably one target point within one horizontal plane by adjusting both bends by way of two actuators.

In one aspect the problem underlying the application is solved by a catheter system for deployment of a medical device, e.g. a replacement heart valve, comprising a steerable sheath according to the disclosure. It may be possible to integrate the steerable sheath in the catheter shaft or integrate the sheath steering points in the catheter outer shaft.

The catheter comprises all components needed for operation and which are well known to the skilled person and thus do not need to be explained in all detail here.

The catheter part carrying the medical device (possible in a capsule, distally) has to be pushed distally of the distal end of the steerable sheath in order to be able to release the medial device. Accordingly, the part carrying the medical device (e.g. a heart valve prosthesis loaded in a capsule) is positioned in the correct level of the native valve.

The double steerable sheath has dimensions in diameter and length which suit the other components like prosthesis, catheter etc. and which are suitable for operating the device and performing delivery and deployment of the prosthesis.

The double steerable sheath has in one aspect an outer diameter of less than or up to 40 French, preferably less than or up to 30 or 20 French or the outer diameter is 18 French. One advantage of the steerable sheath of the disclosure is that the functionality of a reliable deployment of the medical device, e.g. a heart valve prosthesis, can be achieved.

It will be appreciated that higher dimensions in diameter and length of a medical device which has to be operated within a patient's vasculature and bend in different directions represents a challenge in that it requires more force to operate it. Moreover, the parts that are subject to pushing, pulling and bending forces need to be able to stand such increased forces. The higher the dimensions of a device the higher are also such forces on the steerable sheath components.

More so in the disclosed device exhibiting a double bending or S-steering feature the forces acting in different or counter acting directions increase this issue even more.

Accordingly, it was unexpected that the double steering sheath of the disclosure can be operated without any significant issues and that the system can achieve an operability and the task of steering a medical device like a heart valve prosthesis under the increased force requirements in dimensions up to 40 French.

Particularly advantageous is that the functionality is achieved in a double steering sheath in dimensions of up to 40 French or up to 30 French outer diameter. Such a steerable sheath of the disclosure comprises cables as pulling means and the pulling cables are looped through the pull ring at the distal part of the steerable sheath to form the pulling means operated by actuators positioned at the handle.

Such a steerable sheath according to the disclosure is advantageously and surprisingly operable and designed to maintain its functionality of deployment of a medical device, e.g. a heart valve prosthesis. All the components are designed and advantageously work together in a fully functional manner without any significant quality issues or breaking of components.

In particular the steerable sheath of the disclosure achieves the task of reliable deployment of the medical device. In one embodiment the steerable sheath comprises cables which are looped through the pull ring(s), a sheath including a hypotube for performing a predefined bending direction. The components and combination of the components of the steerable sheath according to the disclosure like the hypotube also allows to reduce the bending forces or forces required to direct the distal part of the steerable sheath and/or catheter included therein. The steerable sheath and other components advantageously can withstand and carry the forces exerted on the components of the steerable sheath in connection with pull and push movements, angle bending, stability of the sheath during positioning and deployment of the medical device at the target site and the components of the steerable sheath show good reliability during usage of the steerable sheath.

The selected combination of components of the steering sheath of the disclosure thus achieve advantageous and reliable deployment of the e.g. heart valve prosthesis.

In one aspect the problem underlying the application is solved by a method for deployment of a heart valve prosthesis wherein a steerable sheath according to the disclosure is used and a defined catheter point is actuated to a defined target point.

The method according to the current disclosure can advantageously achieve to position the distal part of the sheath and thus a catheter introduced in various three dimensional directions in a three-dimensional target area. It is thus possible to maneuver the distal sheath and the distal catheter part carrying the medical device with regard to the desired position, level and angle to the target site. Accordingly, a deployment of the medical device with optimized alignment with regard to the native organ, e.g. a heart valve and preferably the annulus or target level, can thus be achieved and an optimized deployment will be possible.

In the method according to the disclosure the actuators are counter-actuated in order to reach various target points within a plane or in a three-dimensional space by adjusting each of the actuators in counter-direction. This is e.g. illustrated in FIG. 15c.

In one aspect of the method according to the disclosure the sheath steering points can be actuated as required to reach a desired target point with the distal part of the steerable sheath or the distal catheter part for a correct and desired deployment and release position, and wherein the actuators are counter-actuated to effect essentially a S-shape of the sheath or a S-shape like geometry of the steering sheath.

In one aspect of the method according to the disclosure the target point can be targeted to comprise the prosthesis or medical device in the catheter perpendicular to the implantation level of the implantation site.

In one aspect of the method according to the disclosure the prosthesis or medical device, e.g. a replacement heart valve, to be deployed is deployed in the native annulus essentially central and/or essentially perpendicular with regard to the native annulus level.

In one aspect the disclosure relates to a method for deployment of a heart valve prosthesis wherein the heart valve is deployed using a steerable sheath according to the disclosure or/and a catheter system as described above or as known by the skilled person.

EXAMPLE

The following is a description of preferred aspects of the disclosure and it shall not be construed to be limiting in any aspect or manner. Moreover, the skilled person will appreciate that any aspect and feature of the disclosure herein above and below can be used and combined with any of the remaining features as disclosed herein. The disclosure shall be understood that any such feature can be combined with any other feature as disclosed herein without being in any sense bound or to be restricted in terms of combination of features.

Example 1

A steerable sheath can comprise in a preferred embodiment the outside part of the sheath comprised of several polymers with varying durometers, On the proximal side of the sheath higher durometer materials are used whereas the durometer of the materials decreases the closer it gets to the distal end. The softer materials on the distal end facilitate bending of the sheath. On the inside the sheath contains a PTFE liner, which reduces friction to the catheter, which is advanced through the sheath. In between the PTFE liner and the polymer jacket a reinforcement structure further influences the behavior of the sheath. Possible reinforcements are braids, coils and laser cut hypotubes. Common materials are metals, mostly stainless steel, but also polymer monofilaments can be used. The design of the reinforcement determines in the distal section the desired bending radius and bending angle and generally the stiffness of each section. The distance of the two sheath steering points is 15 to 90 mm, preferably 70 or 80 mm.

REFERENCE NUMBER LIST 25D material stiffness of Pebax® (=Polyether-Block-Amide-Block-Copolymer=thermoplastic elastomer)
40D material stiffness of Pebax® (=Polyether-Block-Amide-Block-Copolymer=thermoplastic elastomer)
72D material stiffness of Pebax® (=Polyether-Block-Amide-Block-Copolymer=thermoplastic elastomer)
101 unidirectional sheath
102 delivery system/catheter
103 implant/prosthesis
104 implantation site
105 S-shaped sheath (double steerable sheath)
106 target point of distal end of sheath (rectangular to implantation site with distance X)
107 distal bend
108 proximal bend
109 Distal pull ring
110 Cable of distal pull ring
111 Proximal pull ring
112 Cable of proximal pull ring
113 Actuator 1 (actuating cable of distal pull ring)
114 Actuator 2 (actuating cable of proximal pull ring)
115 Laser-cut hypotube
116 Opening of pull ring
Gr Grilamid® (=Polyamide)

The invention claimed is:

1. A steerable sheath comprising
an elongated sheath, two or more actuators including a first actuator and a second actuator, at least two different sheath steering points including a first steering point and a second steering point, means for connecting the first actuator with the first steering point including a proximal cable, and means for connecting the second actuator with the second steering point including a distal cable;
a proximal pull ring including an open ring having two spaced apart ends, the proximal pull ring having an open space between the two ends of the open ring, and a distal pull ring, and the distal cable extending through the open space of the proximal pull ring;
wherein the distal cable extends through a first hole in the distal pull ring and returns in the opposite direction through a second hole in the distal pull ring, so that the distal cable has two parallel portions extending through the open space;
wherein the first steering point bends a first portion of the sheath in a first direction, and the second steering point bends a second portion of the sheath in an opposite direction;
wherein the first steering point is located distal to the second steering point when the steerable sheath is in an undeformed state having a linear orientation;
wherein the first portion of the sheath comprises a first hypotube oriented for bending in the first direction and the second portion of the sheath comprises a second hypotube oriented for bending in the opposite direction;
wherein the first and second steering points are located at least 10° from each other, optionally 10°, 20°, 30°, 45°, 90°, 120°, 140°, 160°, or 180° from each other.

2. The steerable sheath according to claim 1 wherein the first and second actuators independently actuate the first and second steering points.

3. The steerable sheath according to claim 1 wherein the first and second actuators are combined with a proximal handle;
wherein the first hypotube is located distally from the second hypotube, and the bending of the first and second hypotubes forms an S-shaped configuration of the steerable sheath.

4. The steerable sheath according to claim 1 wherein the elongated sheath is made of or comprises a combination of materials selected from biocompatible materials, Polytetrafluoroethylene (PTFE), polymers with differing durometers, stainless steel, nitinol, polyether-block-amide thermoplastic elastomer, or/and a polyamide.

5. The steerable sheath according to claim 1 wherein a first material is used on the distal end of the sheath and a second material harder than the first material is used on the proximal side of the sheath.

6. The steerable sheath according to claim 1 comprising two actuators, two sheath steering points, two means for connecting each of the actuators independently with each one of the sheath steering points.

7. The steerable sheath according to claim 1 wherein each means for connecting can be pulled proximally by way of the first and second actuators.

8. The steerable sheath according to claim 1 wherein the at least two different sheath steering points are spaced circumferential around the sheath or/and longitudinally along the sheath.

9. The steerable sheath according to claim 1 comprising three or four sheath steering points, at different positions along an axis of the steerable sheath.

10. The steerable sheath according to claim 1 wherein the first and second steering points are spaced 1, 2, 3, 4, 5, 6, 7, 8, 9, or 10 cm from each other.

11. The steerable sheath of claim 2, wherein the at least two sheath steering points allow a longitudinal direction at the distal end of the sheath to be perpendicular to an implantation site.

12. The steerable sheath of claim 11, wherein the first and second steering points are longitudinally spaced about 15 to 90 mm from each other and circumferentially spaced about 180° from each other.

13. The steerable sheath of claim 11, wherein the first steering point bends the first portion of the sheath by an arc of greater than 90°, wherein the first portion of the sheath is distal relative to the second portion of the sheath.

14. The steerable sheath of claim 1, wherein the first and second steering points are located 180° from each other and spaced 5 to 10 cm from each other; and
wherein a softer material is used on the distal end of the sheath and a harder material on a proximal side of the sheath; and
wherein the first and second actuators are combined with a proximal handle.

15. The steerable sheath of claim 1, wherein each of the first and second hypotube includes a spine extending in an axial direction of the steerable sheath and connecting spaced apart rings, wherein the spine of the first hypotube is oriented 10°, 20°, 30°, 45°, 90°, 120°, 140°, 160°, or 180° relative to the spine of the second hypotube.

16. A steerable sheath comprising:
an elongated sheath,
at least one actuator,
at least two different sheath steering points,
means for connecting the at least one actuator with the at least two different sheath steering points;
wherein the means for connecting comprises a proximal cable and a distal cable:
a proximal pull ring including an open ring having two spaced apart ends, the proximal pull ring having an open space between the two ends of the open ring, and a distal pull ring, and the distal cable extending through the open space of the proximal pull ring;
wherein the distal cable extends through a first hole in the distal pull ring and returns in the opposite direction through a second hole in the distal pull ring, so that the distal cable has two parallel portions extending through the open space;
wherein the at least two sheath steering points includes a first steering point for bending a first portion of the sheath in a first direction, and a second steering point for bending a second portion of the sheath in an opposite direction,
wherein the steering points allow a distal end of the sheath to be positioned both with respect to:
a) its distance from an implantation sitei and;
b) its angle relative to the implantation site;
wherein the first and second steering points are located 180° from each other and spaced 5 to 10 cm from each other;
wherein the first portion of the sheath comprises a hypotube oriented for bending in the first direction, wherein the hypotube includes a spine connecting spaced apart rings;
wherein the first steering point bends the first portion of the sheath by an arc of greater than 900, wherein the first portion of the sheath is distal relative to the second portion of the sheath.

17. The steerable sheath according to claim 16,
wherein the at least one actuator comprises a first actuator and a second actuator,
wherein the first and second actuators are counter-acting actuators;
wherein the first and second steering points are counter-acting movable by way of the counter- acting actuators;
wherein the counter-acting actuators allow the distal end of the sheath to reach various target points within one horizontal plane by adjusting both the bending of the first portion of the sheath and the bending of the second portion of the sheath by way of the first and second actuators.

18. A catheter system for deployment of a heart valve prosthesis comprising the steerable sheath according to claim 1.

19. A method comprising the steps of:
initiating deployment of a heart valve prosthesis at a defined target point with the steerable sheath according to claim 1, wherein the defined target point is sufficiently spaced from an implant site for fully deploying the prosthesis
adjusting at least the first and second actuators for controlling the distance from the distal end of the steerable sheath to the implant site and the angle of the distal end;
optionally wherein the first and second actuators are counter-actuated in order to reach various target points within one horizontal plane by adjusting each of the actuators in counter-direction.

20. A method for deployment of a heart valve prosthesis wherein the heart valve prosthesis is deployed using the steerable sheath according to claim 1.

21. A method for deployment of a heart valve prosthesis wherein the heart valve prosthesis is deployed using the catheter system according to claim 18.

22. A steerable sheath comprising an elongated sheath wherein the steerable sheath includes a proximal pull ring including an open ring having two spaced apart ends, the proximal pull ring having an open space between the two ends of the open ring and a distal pull ring, and a distal cable extending through the open space of the proximal pull ring; wherein the distal cable extends through a first hole in the distal pull ring and returns in the opposite direction through a second hole in the distal pull ring, so that the distal cable has two parallel portions extending through the open space.

23. The steerable sheath of claim 22, wherein the two parallel portions are arranged less than 10° from each other.

24. The steerable sheath of claim 22, wherein the two parallel portions bend a section of the sheath in the same direction.

25. A catheter system for deployment of a heart valve prosthesis comprising the steerable sheath according to claim 22.

* * * * *

UNITED STATES PATENT AND TRADEMARK OFFICE
CERTIFICATE OF CORRECTION

| | | |
|---|---|---|
| PATENT NO. | : 11,925,555 B2 | |
| APPLICATION NO. | : 16/640180 | |
| DATED | : March 12, 2024 | |
| INVENTOR(S) | : Nadine Stappenbeck and Helmut Straubinger | |

It is certified that error appears in the above-identified patent and that said Letters Patent is hereby corrected as shown below:

In the Claims

Column 15, Line 26, replace "a) its distance from an implantation sitei and;" with --a) its distance from an implantation site; and--

Signed and Sealed this
Seventh Day of May, 2024

Katherine Kelly Vidal
*Director of the United States Patent and Trademark Office*